United States Patent
Kawamura et al.

(10) Patent No.: US 7,128,348 B2
(45) Date of Patent: Oct. 31, 2006

(54) FEMALE CONNECTOR

(75) Inventors: Shin-ichi Kawamura, Osaka (JP); Takahito Wakabayashi, Osaka (JP); Masato Hidaka, Osaka (JP); Takayuki Deguchi, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 11/029,537

(22) Filed: Jan. 6, 2005

(65) Prior Publication Data

US 2005/0146136 A1 Jul. 7, 2005

(30) Foreign Application Priority Data

Jan. 7, 2004 (JP) ............... 2004-001789

(51) Int. Cl.
*F16L 25/00* (2006.01)
*A61M 39/10* (2006.01)

(52) U.S. Cl. ............... 285/332; 285/332.1; 604/533; 604/534; 604/535

(58) Field of Classification Search ........... 285/332, 285/332.1; 604/533, 534, 535, 905
See application file for complete search history.

(56) References Cited

U.S. PATENT DOCUMENTS

| | | | | |
|---|---|---|---|---|
| 4,547,194 A | * | 10/1985 | Moorehead | 604/523 |
| 4,824,145 A | * | 4/1989 | Carlsson | 285/38 |
| 4,991,629 A | * | 2/1991 | Ernesto et al. | 138/89 |
| 5,286,067 A | * | 2/1994 | Choksi | 285/38 |
| 5,312,377 A | * | 5/1994 | Dalton | 604/534 |
| 5,464,400 A | * | 11/1995 | Collins | 604/538 |
| 5,651,776 A | * | 7/1997 | Appling et al. | 604/534 |
| 6,165,149 A | * | 12/2000 | Utterberg et al. | 604/5.01 |
| 6,620,119 B1 | * | 9/2003 | Utterberg et al. | 604/5.01 |
| 2002/0062106 A1 | * | 5/2002 | Chu et al. | 604/167.01 |
| 2003/0158539 A1 | * | 8/2003 | Bouphavichith et al. | 604/533 |
| 2004/0039373 A1 | * | 2/2004 | Harding et al. | 604/533 |
| 2005/0010195 A1 | * | 1/2005 | Bouphavichith et al. | 604/533 |

FOREIGN PATENT DOCUMENTS

| | | |
|---|---|---|
| EP | 0 248 979 A1 | 12/1987 |
| EP | 0 775 501 A1 | 5/1997 |
| EP | 0 941 743 A2 | 9/1999 |
| EP | 0 953 365 A2 | 11/1999 |
| JP | 11-313896 | 11/1999 |

* cited by examiner

*Primary Examiner*—James M. Hewitt
(74) *Attorney, Agent, or Firm*—Kubovcik & Kubovcik

(57) ABSTRACT

A female connector including: a cylindrical core member having a luer taper on a distal inner surface thereof and a tube bonding portion formed on a proximal end inner surface and being formed with a flange at a distal extremity thereof; a cylindrical housing having a male screw formed on an outer surface thereof and mounted to an outer periphery of the core member without being fixed, and a stopper fixed at a position apart from the flange of the core member, wherein the distance (L1) between the flange and the stopper is larger than the length (L2) of the housing in the axial direction when a male connector is connected to the female connector.

5 Claims, 2 Drawing Sheets

FEMALE CONNECTOR

BACKGROUND OF THE INVENTION

The present invention relates to a female connector to be provided at an end of a medical tube which is used for guiding, or introducing, a fluid and includes various tubes for blood circuits, or blood-supply or infusion tubes, and various catheter tubes. More specifically, the invention relates to a female connector in which a risk of inadvertent disconnection after being connected to a male connector is reduced.

A female connector provided on a medical tube for guiding a fluid is capable of connecting to a male connector provided on another tube or on an instrument. The female connector is formed with a specified female luer taper on an inner surface thereof, and with a specified male screw on an outer surface thereof. On the other hand, the male connector has a concentric dual cylindrical shape and is formed with a specified male luer taper on an outer surface of an inner cylinder, and with a specified female screw on an inner surface of an outer cylinder. Liquid-tightness or air-tightness of a connected portion between the female connector and the male connector is ensured by screwing the male screw of the female connector to the female screw of the male connector and by fitting the female luer taper of the female connector to the male luer taper of the male connector.

In the related art, when the female connector is connected to the male connector, the female connector is inserted onto the male connector while being screwed. Consequently, a tube connected to the female connector is twisted and its usability is impaired, and sometimes the female connector is disconnected from the male connector with the force of the twisted tube returning to its straight form. There is also a problem that when a load is exerted on the wings, which are provided for facilitating a tightening operation, in the direction of loosening the screw, liquid-tightness or air-tightness at the connected portion between the female connector and the male connector is immediately impaired.

As a measure for solving the twisting problem of the tube, female connectors which are divided into two parts, a core member and a housing member which are rotatable with respect to each other are already disclosed (European Patent No.0775501 and Japanese Patent Laid-Open No.313896/1999). With these female connectors, the twisting problem of the tube when the female connector is connected to the male connector is solved, and the risk of disconnection between both connectors due to the force of the twisted tube tending to restore straightness can be reduced.

However, with the female connectors of the prior art, in order to fit a recess on a housing and a projection on a core member to prevent disconnecting of the tube in an axial direction, the hardness of the core member must be selected. In order to do so, it is necessary to carefully select a material in order to form a core member which coheres to the male luer taper.

In addition, in order to establish a female connector having such a structure that the tube is not disconnected in the axial direction, a processing step to moderately soften the core member by heating during manufacturing is necessary. However, setting of conditions so that the core member is softened and deformed and the original shape of the core member is restored after being inserted into a housing is extremely difficult.

In the structure described above, the problem that liquid-tightness or air-tightness is impaired when a load which acts to loosen the screwing is exerted on the wings provided on the housing is not solved, and it is insufficient as a measure for preventing the tube from being disconnected.

SUMMARY OF THE INVENTION

In view of the above-described problems, intense studies were carried out and it was determined that a female connector including a core member, a housing attached to an outer periphery of the core member, and a stopper fixed at a predetermined position apart from the core member, wherein the distance (L1) between a flange provided on the core member and the stopper is equal to or larger than the overall length (L2) of the housing in the axial direction have an outstanding effect in preventing tube disconnection, and the present invention was completed.

In other words, the present invention relates to a female connector including: a cylindrical core member including a luer taper on an inner surface of a distal end portion thereof, a tube bonding portion on an inner surface of a proximal end portion thereof, and a flange at a distal extremity thereof; a cylindrical housing having a male screw formed on an outer surface thereof and mounted on an outer periphery of the core member without being fixed; and a stopper fixed to the core member at a predetermined position apart from the flange, wherein the distance (L1) between the flange and the stopper is equal to or larger than the overall length (L2) of the housing 2 in the axial direction.

According to the present invention, the housing is free to rotate with respect to the core member. Therefore, a fluid guiding tube connected to the female connector is not twisted even though the female connector is connected to a male connector.

Besides, the fitting between the female luer taper of the female connector and the male luer taper of the male connector does not easily come apart even when a load for loosening the screw is inadvertently exerted on the wings provided on the housing. Therefore, occurrence of an accidental disconnection between the female connector and the male connector can be extremely reduced, and the fitted state can be released as needed.

DESCRIPTION OF THE DRAWINGS

The female connector of the present invention is described in detail below by referring to preferred embodiments shown in the appended drawings. However, the present invention is not limited to these embodiments.

DETAILED DESCRIPTION OF THE INVENTION

Figure 1:
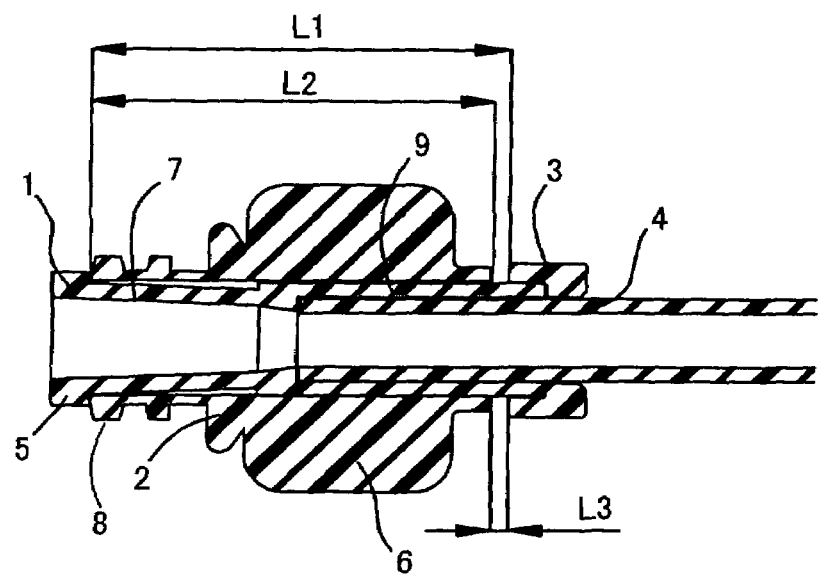
FIG. 1 is a cross-sectional view of the female connector according to an embodiment of the present invention.

The female connector of the present invention includes a core member 1, a housing 2 mounted on the outer surface of the core member 1, and a stopper 3 fixed at a predetermined position apart from a flange 5 of the core member 1.

The core member 1 has a cylindrical shape, and is formed with a female luer taper 7 of, for example, 6/100, at a distal end portion. The female luer taper 7 is adapted to be fitted with a male luer taper of a male connector inserted therein. A flange 5 for limiting a distance of forward movement of the housing 2 is provided at a distal extremity of the core member 1. The core member 1 has a tube bonding portion 9 on an inner surface at a proximal end portion thereof, to which a fluid guiding tube 4 is fixed by bonding. The core member 1 and the fluid guiding tube 4 are each formed of a soft material such as vinyl chloride, polyurethane, or polybutadiene.

The housing 2 also has a cylindrical shape, and is formed with a male screw 8 on an outer surface at a distal end portion thereof. The housing 2 is formed with wings 6 on an outer surface thereof for improving the operability during the tightening operation. The housing 2 is mounted in the coaxial direction on an outer periphery of the core member 1, but is not fixed. The housing 2 is preferably formed of a hard material such as polypropylene or polycarbonate.

The stopper 3 is fixed at a predetermined position apart from the flange 5 of the core member 1. It is not necessary to specifically select, or limit, the hardness of the stopper 3 in order to satisfy its function, and materials which are easy to bond to other parts of female connector are preferable.

Figure 2:
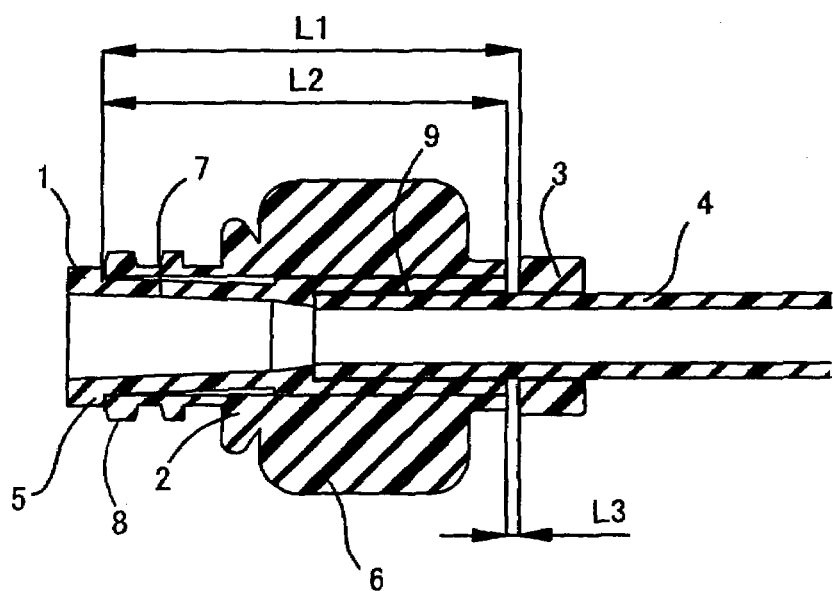
FIG. 2 is a cross-sectional view of the female connector according to another embodiment of the present invention.
Figure 3:
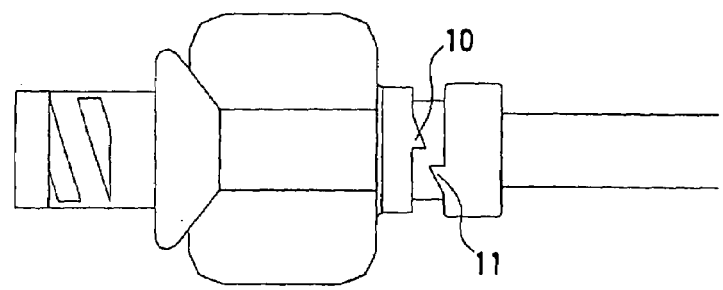
FIG. 3 is a front view of the female connector according to still another embodiment of the present invention.

The stopper 3 also has a cylindrical shape, and may be formed with a step or the like on an inner surface or an outer surface so that positioning during manufacturing is facilitated. The stopper 3 may be fixed to the proximal end portion of the core member 1 as shown in FIG. 1, or may be fixed by bonding to the fluid guiding tube 4 as shown in FIG. 2. In addition, as shown in FIG. 3, a projection 10 is preferably formed on the housing 2 at an end toward the stopper 3, and an engagement portion 11 which can engage with the projection 10 is formed on the stopper 3 at an end toward the housing 2.

The present invention is characterized in that a length, or distance, (L1) between the proximal end of flange 5 and the distal end of stopper 3 of the female connector is equal to or larger than the overall length (L2) of the housing 2 in the axial direction as shown in FIG. 1 or FIG. 2. The overall length (L2) (hereinafter simply referred to as the length) of the housing 2 in the axial direction is normally from 10 to 60 mm, and preferably from 20 to 50 mm.

The length of the core member in the axial direction is normally from 10 to 60 mm, and preferably, from 20 to 50 mm. The length of the flange 5 in the axial direction is normally from 0.5 to 5 mm, and preferably, from 1 to 4 mm. The length of the stopper 3 in the axial direction is normally from 1 to 10 mm, and preferably from 2 to 7 mm.

The length (L1) between the flange 5 and the stopper 3 is set based on the length (L2) of the housing 2, a screwing length of a screw portion and pitches thereof, and a change of dimensions of the respective parts when the male connecter is connected.

When the male connector is not connected, the length (L1) between the flange 5 and the stopper 3 is equal to or larger than the length (L2) of the housing 2, and is normally from 10 to 60 mm, and preferably from 20 to 50 mm. On the other hand, when the male connector is connected, the length (L1) is consequently larger than the length (L2) of the housing 2 since the core member 1 formed of a soft material is extended as described below. The difference between the length (L1) and the length (L2) when the male connector is connected, that is, the length (L3) between the proximal end of the housing 2 and the distal end of the stopper 3, is preferably 0.5 to 6 mm.

It is not suitable for the length (L1) between the flange 5 of the housing 2 and the stopper 3 to be equal to the length (L2) of the housing 2 when the female connector is connected to the male connector. When the length (L1) between the flange 5 of the housing 2 and the stopper 3 is equal to the length (L2) of the housing 2 in the axial direction in a state in which the female connector is connected to the male connector, the proximal end of the housing 2 contacts the stopper 3. If a load for screwing down is exerted on the wings 6, the housing 2 pushes the core member 1 in the opposed direction toward the male connector. Accordingly, the fitting between the female luer taper 7 and the male luer taper easily comes apart and the liquid-tightness or the air-tightness at the connected portion between the connectors may be impaired.

It is not suitable for the length (L3) between the proximal end of the housing 2 and the distal end of the stopper 3 to be too large when the female connector is disconnected from the male connector. If the length (L3) between the proximal end of the housing 2 and the distal end of the stopper 3 is too large, when the female connector is disconnected from the male connector, only the male screw 8 of the housing 2 is unscrewed from the female screw of the male connector and the fitting between the female luer taper 7 of the core member 1 and the male luer taper of the male connector cannot come apart.

When the female connector of the present invention is connected to the male connector, the female luer taper is fitted to the male luer taper by a force exerted on the wings 6 of the housing 2 and screwing the male screw 8 to the female screw of the male connector. At that moment, the female luer taper 7 is fitted tightly to the male luer taper because the distal end portion of the housing 2 pushes the flange 5 of the core member 1 toward the male connector.

Figure 4:
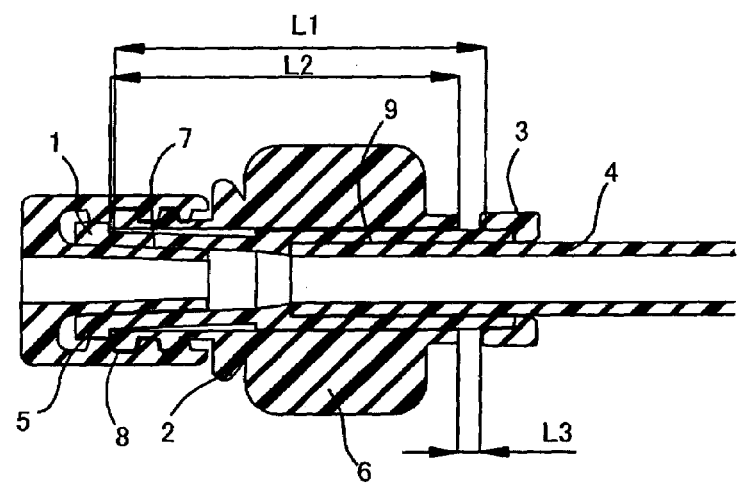
FIG. 4 is a cross-sectional view illustrating a state in which the female connector shown in FIG. 1 is fitted to a male connector.

When the female luer taper 7 is cohered to the male luer taper, it is hard for the core member 1 to advance any more toward the male connector. Thereon, a further attempt to screw the male screw 8 to the female screw causes the core member 1 formed of a soft material to deform and the length of the core member 1 is increased. Consequently, the length (L1) between the flange 5 and the stopper 3 on the female connector becomes larger than before connecting to the male connector (FIG. 4).

Figure 5:
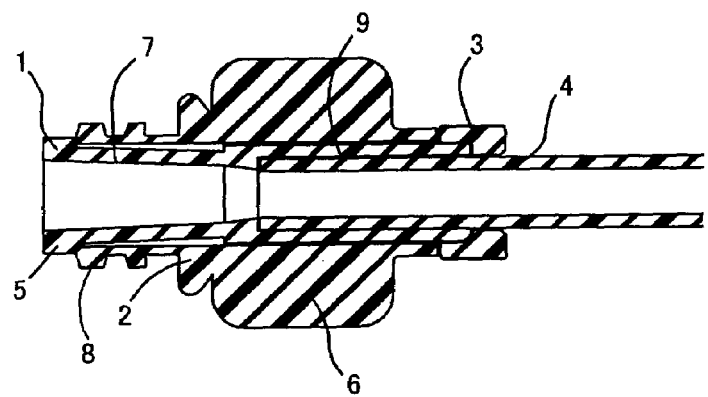
FIG. 5 is a cross-sectional view showing the female connector according to a still further embodiment of the present invention.

Therefore, even when the length (L1) between the flange 5 and the stopper 3 is equal to the length (L2) of the housing 2 (FIG. 5) before connecting to the male connector, the effect of the present invention is achieved as long as the length (L1) between the flange 5 and the stopper 3 is larger than the length (L2) when the male connector is connected.

In the present embodiment, the difference between the length (L1) and the length (L2) when the male connector is connected, that is the length (L3) between the housing 2 and the stopper 3, is preferably smaller than the screwing distance of a screw portion. The screwing distance of a screw portion as used herein means a screwing distance of the male screw 8 into the female screw, more specifically, a linear axial distance from a position of initiation of screwing between the male screw 8 and the female screw to a final position of screwing of the male screw into the female screw.

The core member 1, the housing 2, and the stopper 3 are manufactured by injection molding, and the fluid guiding tube 4 is manufactured by extrusion molding. First, the core member 1 is inserted into the housing 2 without fixing to the inner surface of the housing 2, and then the stopper 3 is fixed to a proximal end portion of the core member 1 sticking out from a proximal side of the housing 2 by bonding.

Subsequently, the fluid guiding tube 4 is bonded to the tube bonding portion 9 of the core member 1. At this time, the fluid guiding tube 4 may be bonded to the stopper 3 together with the core member 1. Fixation of the stopper 3 at a predetermined position apart from the flange 5 of the core member 1 may be done by bonding directly to the core member 1 or, as shown in FIG. 2, bonding with respect to the core member 1 via the fluid guiding tube 4 or the like.

Also, as shown in FIG. 3, connection between the female connector and the male connector may be easily released by providing a projection 10 at an end of the housing 2 toward the stopper and providing an engagement portion 11 which can engage with the projection 10 at an end of the stopper 3 toward the housing 2.

Namely, when a load for screwing down is exerted on the wings 6 of the housing 2, the projection 10 is engaged with the engagement portion 11. Therefore, a force exerted on the wings 6 which moves the housing 2 toward the stopper 3 is also exerted on the stopper 3 and the core member 1 fixed to the stopper 3, so that the fitting between the female luer taper 7 and the male luer taper comes apart easier.

The present application claims priority of Japanese patent application No. 2004-001789, the disclosure of which is incorporated herein by reference.

What is claimed is:

1. A female connector to be connected to a fluid delivery tube comprising:
   a cylindrical core member including a luer taper on an inner surface of a distal end portion of the core member, a tube bonding portion on an inner surface of a proximal end portion of the core member, and a flange at a distal end of the core member;
   a cylindrical housing mounted to an outer periphery of the core member without being fixed and having a male screw formed on an outer surface of the housing; and
   a stopper fixed at a predetermined position apart from the flange of the core member,
   wherein a distance (L1) between the flange and the stopper is equal to or larger than a length (L2) of the housing in an axial direction and a length (L3) between a proximal end of the housing and a distal end of the stopper when the female connector is connected to a male connector is smaller than a screwing distance of the male screw of the female connector into a female screw of the male connector.

2. A female connector according to claim 1, wherein the distance (L1) between the flange and the stopper is larger than the length (L2) of the housing in the axial direction when the female connector is connected to a male connector.

3. A female connector according to claim 1, wherein a projection is formed at an end of the housing facing the stopper and an engagement portion which can engage with the projection is formed at an end of the stopper facing the housing.

4. A female connector according to claim 1, wherein the housing includes wings on an outer surface of the housing.

5. A female connector according to claim 1, wherein the core member is formed of one material selected from the group consisting of vinyl chloride, polyurethane and polybutadiene and the housing is formed of one material selected from the group consisting of polypropylene and polycarbonate.

* * * * *